United States Patent [19]

Hood et al.

[11] Patent Number: 4,816,017
[45] Date of Patent: Mar. 28, 1989

[54] ULTRASONIC DECOUPLING SLEEVE

[75] Inventors: Larry L. Hood, Laguna Hills; Maurice M. Imonti, Dana Point, both of Calif.

[73] Assignee: CooperVision, Inc., Palo Alto, Calif.

[21] Appl. No.: 40,812

[22] Filed: Apr. 21, 1987

Related U.S. Application Data

[62] Division of Ser. No. 822,277, Jan. 24, 1986, Pat. No. 4,681,561.

[51] Int. Cl.4 ............................................... A61F 2/32
[52] U.S. Cl. ..................................... 604/22; 128/305; 433/119
[58] Field of Search ............... 604/22, 27, 28, 30, 604/35, 43, 44, 46, 167, 169, 282; 128/305, 24 A; 433/119; 283/399

[56] References Cited

U.S. PATENT DOCUMENTS

| Re. 30,536 | 3/1981 | Perdreaux, Jr. | 433/119 |
|---|---|---|---|
| 3,693,613 | 9/1972 | Kelman | 128/24 A |
| 3,805,787 | 4/1974 | Banko | 128/276 |
| 3,945,375 | 3/1976 | Banko | 604/22 |
| 3,990,453 | 11/1976 | Douvas et al. | 128/305 |
| 4,011,869 | 3/1977 | Seiler, Jr. | 604/22 |
| 4,200,106 | 4/1980 | Douvas et al. | 128/305 |
| 4,316,465 | 2/1982 | Dotson, Jr. | 128/276 |
| 4,417,578 | 11/1983 | Banko | 604/22 |
| 4,428,748 | 1/1984 | Peyman et al. | 604/22 |
| 4,504,264 | 3/1985 | Kelman | 604/27 |
| 4,515,583 | 5/1985 | Sorich | 604/22 |
| 4,634,420 | 1/1987 | Spinosa et al. | 604/22 |
| 4,643,717 | 2/1987 | Cook et al. | 604/22 |
| 4,681,561 | 7/1987 | Hood et al. | 604/22 |

Primary Examiner—Stephen C. Pellegrino
Assistant Examiner—Mario Costantino
Attorney, Agent, or Firm—Vorys, Sater, Seymour and Pease

[57] ABSTRACT

A decoupling sleeve for inclusion in a fluid conduit of an ultrasonically-operated instrument, such as a surgical instrument, which is irrigated by irrigating fluid at the operative site. The decoupling sleeve includes a tubular thin-walled body portion defining spaced openings, and a collar member for retaining the decoupling sleeve in a tip cap sleeve member for the instrument. The inclusion of the decoupling sleeve in the irrigating fluid conduit intermediate a portion of an ultrasonically-operated tool and the interior of the tip cap sleeve member defining the fluid conduit impedes the transmission of ultrasonic energy through the fluid medium in the conduit, thus reducing objectionable cavitation and bubble formation at the operative site.

52 Claims, 2 Drawing Sheets

ULTRASONIC DECOUPLING SLEEVE

This is a divisional of application Ser. No. 822,277 filed on Jan. 24, 1986, now U.S. Pat. No. 4,681,561.

BACKGROUND OF THE INVENTION

This invention relates generally to fluid-irrigated, ultrasonically-operated cutting devices, and particularly to surgical instruments of the type which employ ultrasonic energy for operating on tissue. This invention especially relates to an ultrasonic decoupling sleeve interposed in a fluid passage to improve the operating characteristics of a surgical device in a surgical irrigation-aspiration apparatus, such as is used in eye surgery.

Surgical instruments utilizing ultrasonic vibrations in combination with the circulation of irrigation liquid over the operative site for the removal of tissue from a biological body are well known and widely used, particularly in enclosed and substantially enclosed operative sites. Such surgical instruments are particularly well adapted for the removal of cataracts and other surgical procedures performed on the eye. Ultrasonic surgical instruments of the type with which the present invention is primarily concerned conventionally employ an elongated probe or operative tip having an end rigidly attached through a vibration transmissive member to a transducer for supplying ultrasonic energy to the other or free end of the probe. The ultrasonic energy is emitted to dislodge and break-up or emulsify tissue from the operative site for removal by aspiration. Irrigating fluid is delivered through a shield, or sheath, surrounding the body of the probe for discharge adjacent to the tip or free end of the probe and is returned by suction through a hollow center of the tubular body of the probe. An ultrasonic surgical aspirator of this type is shown in U.S. Pat. No. 3,805,787 as including conduits for applying suction through the center of the vibration transmitting operative probe and for supplying irrigating fluid around the outer surface of the probe through a passage defined by a tubular shield. The irrigation fluid flows around the free end of the probe element and back through the center of the probe to effectively irrigate and remove discharged and emulsified tissue. Various shield arrangements for controlling or directing the flow of irrigating fluid in the vicinity of the free end of the operative probe are shown in that prior patent, as well as in U.S. Pat. Nos. 3,693,316 and 4,515,583.

Significant attention in the art for improving the operative characteristics of those devices for the convenience of the surgeon and to enhance the efficacy of the instrument for the safety of the patient has been directed to solving a number of problems. For example, it has been proposed to form the ultrasonic rigid tip cap sleeve in one piece, or as a transparent member and to provide devices which can accommodate increasingly smaller incisions. Such sleeve components defining the irrigation fluid conduit passages of those instruments have, however, sometimes channeled cavitation bubbles caused by the ultrasonically-vibrating member and as a result of directing the irrigating fluid around the ultrasonic tip. Those cavitation bubbles create a visual obstruction in delicate surgery, and an annoyance in the eye during surgery. Usually the surgeon is required to interrupt the surgery to permit the aspiration system to remove the bubbles before resuming the surgery.

Such caviation and bubbles may also adversely affect the stability of the ultrasonic action during surgery. For example, it is a consistent desire in the production of such instruments to provide power consistently to the ultrasonically vibrated tip without power fall-offs or surges so that the surgeon can expect the ultrasonic power delivered by the tip during the surgical procedure to be conveniently consistent and thus minimize his attention to fluctuations and variations in the operative characteristics of the instrument. It is believed that the presence of such cavitation bubbles has an effect on the stability of the instrument in creating variations in the mechanical impedance in the instrument which causes corresponding variations in the mechanical operating characteristics of the instrument. Accordingly, it is desired to decouple and isolate the operative tip from the outer shell and to avoid cavitation bubbles in the fluidic path in order to preclude power drop-off and reduce instability in the operative characteristics of the instrument.

It is thus a general object of this invention to improve an instrument of the type described by improving its stability and by reducing or eliminating cavitation of and bubble formation in the irrigating fluid.

It is also a general aim in the art to improve load isolation, acoustical and hydraulic pressure confinement, and to achieve sound reduction and load stabilization in connection with such instruments.

SUMMARY OF THE INVENTION

Directed to achieving the foregoing objects of this invention and overcoming the problems associated with prior instruments, while improving the operative characteristics of such instruments, the invention relates to an improvement in the aspiration and irrigating fluid conduit of an ultrasonically operated surgical instrument of the type having an elongated generally cylindrical handpiece containing an irrigation supply conduit and having at one end an elongated tubular aspiration fluid conduit wherein the irrigation fluid conduit comprises a hollow body having walls surrounding an axis, a first end open for fluid transmissive communication with the supply conduit, and a second end having an axial opening therein, the hollow body portion having means for engaging the handpiece, and a tubular sleeve portion in fluid transmission communication with the axial opening in the second end and coaxially extending therefrom. The improvement according to the invention comprises a component for use in such combination which comprises a tubularly-shaped decoupling member made from a rigid or semi-rigid material preferably defining fluid passages in the form of holes or slots at a distal end of a wall thereof. The tubularly-shaped member is axially interposed in the irrigating fluid passage intermediate the tip cap sleeve and the operative portion of the instrument to enhance the propoerties of the tip cap sleeve and reduce the amount of cavitation and bubbles occurring with the use of such tip cap sleeve but without the addition of the decoupling component according to the invention. The decoupling member stabilizes ultrasonic action during surgery, particularly during eye surgery. The decoupling sleeve, when so used, thus acts to impede the transmission of ultrasonic energy through the fluid in the fluid conduit to the instrument, rather than to the tip. The decoupling sleeve may also improve the laminar flow characteristics of the fluid conduit for irrigating fluid, further reducing a tendency toward bubble formation and cavitation.

Preferably, the tubular component or decoupling sleeve comprises a generally cylindrical, thin walled body portion defining oppositely-spaced openings 180 degrees apart on the diametrically opposed sides thereof. The openings, in the form of slots, are defined by an axial length terminating in semicircularly-shaped opposed end portions. The axially-extending decoupling sleeve terminates in a collar portion having an outside diameter slightly larger than the outside diameter of the axially-extending portion, to cause the decoupling sleeve to be retained in the tip cap sleeve member. The decoupling sleeve according to the invention is arranged to float freely on the interior of the tip cap sleeve member or infusion sleeve, while an axially-extending portion of the vibrator tip extends through its interior.

The drawings are illustrative of the concept of the invention and should not unduly limit the invention which obviously could include other embodiments obvious to a person of ordinary skill in the art within the spirit of the invention.

DETAILED DESCRIPTION OF THE PREFERRED EMBODIMENT

Figure 1:
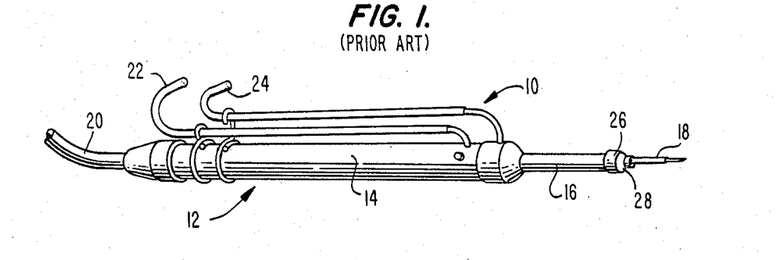
FIG. 1 depicts a conventional ultrasonic surgical irrigator-aspirator of the type which incorporates a tip cap sleeve member which acts as an irrigation conduit.

The conventional ophthalmological surgical tool which incorporates coaxial irrigation and aspiration functions to which the decoupling sleeve according to this invention is particularly applicable is designated generally by the reference numeral 10 in FIG. 1. A surgical tool 10 of this type comprises a handpiece shown generally at the reference numeral 12, having an elongated gripping or barrel portion 14 and an extension 16 which supports an ultrasonically-vibrated surgical tool or needle 18. The handpiece 12 is provided with a conduit 20 containing power and control leads and cooling water tubes for cooling the handpiece. The tool 10 is also provided with an aspiration conduit 22 which is connected to a source of vacuum and an irrigation conduit 24 connected to a source of irrigation fluid. Both conduits 22 and 24 are connected to passages within the handpiece 12 leading to the region of the extension 16 of the handpiece. The distal end of the handpiece 12 is provided with an a tip cap 26 and a tip cap sleeve member 28 which surrounds the ultrasonic tool 18 and provides a coaxial annular passage for supplying irrigation fluid to the surgical site at the tip of the tool 18.

Figure 2:
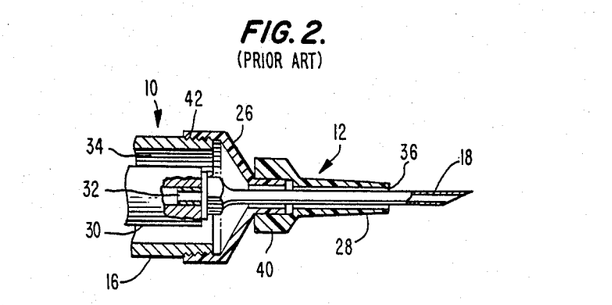
FIG. 2 shows a longitudinal cross section of the tip portion of the conventional irrigator-aspirator of FIG. 1, showing the attachment of the tip cap sleeve member to the handpiece in a prior art arrangement.

FIG. 2 shows a detailed longitudinal cross-section of the distal end of the handpiece 12. The ultrasonic tool 18 is fastened to the ultrasonically-vibrating connecting member 30 by a threaded connection. An axial bore 32 in the ultrasonic tool 10 communicates with the aspiration line 22 through conventional drilled passages in the ultrasonic connecting member 30 and the handpiece (not shown). The region between the ultrasonic connecting member 30 and the extension 16 provides a conduit 34 for irrigation fluid. The irrigation fluid conduit is connected by conventional channels (not shown) in the handpiece 12 to the irrigation fluid line 24. The sleeve member 28 surrounds the ultrasonic tool 18 to provide a coaxial fluid channel 36 which receives fluid from the fluid channel 34 and conveys it to the surgical site.

The sleeve member 28 is hollow and has a body portion 40 which is connected to the tip cap 26, which has means for engaging the front end of the surgical instrument 10 so as to be in fluid communication with the passage or passages in the handpiece which supply irrigation fluid. The body portion 40 of the sleeve member 28 surrounds the ultrasonically vibrating tool 18 and has an axis which is coincident with the axis of the ultrasonically vibrated tool. Generally, the body portion is cylindrical in shape and has a relatively thick wall provided with fastening means at one end of the body for connecting to the tip cap 26. The combination of the tip cap 26 and the body portion 40 of the sleeve member 28 engage the handpiece 10 to be retained thereon. Preferably, mechanical fastening means are internal threads 42 on the interior wall of the body portion 40 which threadably engage external threads on the end of the handpiece 10 to fasten the tip cap 26 and the sleeve 28 thereto.

The body member 40 and sleeve 28 are usually moulded homogeneously from one synthetic resin material. The distal tip of the fluid conduit is sized to fit closely over the aspiration member of a surgical irrigator/aspirator and is provided with a tapered section for easy insertion into an incision. Side infusion openings are also formed in the sleeve member to provide free flow of irrigation fluid to the surgical site.

Figure 3:
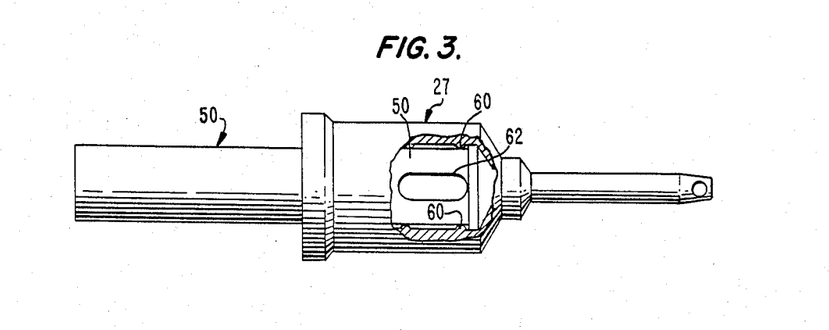
FIG. 3 illustrates in a partially broken-away view, the addition of a decoupling sleeve according to the invention in the fluid conduit in the tip portion of the irrigator-aspirator intermediate the tip cap sleeve member and the axially-extending tip.
Figure 4:
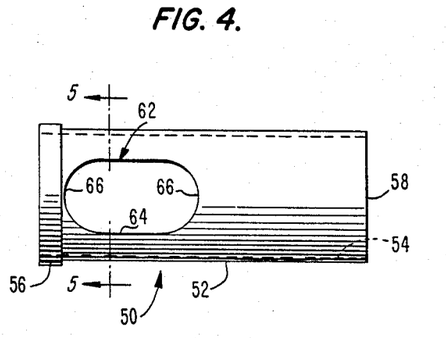
FIG. 4 shows a side elevational view of the decoupling sleeve according to the invention illustrating its slot arrangement and collar.

FIG. 3 shows the improvement according to the invention wherein a decoupling sleeve 50, to be described in greater detail in connection with FIG. 4, is interposed within the confines of the infusion sleeve 27 and, more particularly, in the fluid passage thereof. Similarly, the decoupling sleeve 50 is located within the confines of the combination of the tip cap 26 and the sleeve member 28 when a two-piece construction, as shown in FIGS. 1 and 2, is used. The decoupling sleeve 50, as shown in FIG. 4, comprises an elongated, axially-extending thin-walled tubular member 52 defining an axially-extending bore 54 therethrough. The axially-extending tubular member 52 terminates in a collar 56 having an outside diameter slightly greater than the outside diameter of the tubular member 52. Normally, the outer and inner dimensions of the decoupling sleeve 50 relative to the enveloped outside dimension of the vibrating member and the inside dimension of the infusion sleeve 27 permit irrigation fluid passage along both the interior and exterior surfaces of the decoupling sleeve 50. However, the outside dimension of the sleeve 50 may be sufficiently large to cause the outer surface of the tubular member 52 to rest against the inner surface of the infusion sleeve 27. In that case, the irrigation fluid passage is confined to the interior of the decoupling sleeve 50. Conversely, the inside dimension of the sleeve 50 may, in an extreme, be slightly larger than the outer dimension of the through-passing portion of the tool, causing the irrigation fluid passage to be located entirely on the outside of the decoupling sleeve 50.

The decoupling sleeve 50 may be made from a rigid material, such as a plastic or metal and preferably from polypropylene, or from a semi-rigid material such as silicon tubing. When so constituted, the sleeve 50 may be made by moulding, extruding, or forming into a tubular shape. While the sleeve 50 is preferably cylindrical in overall shape to fit conveniently in the cylindrical fluid passage, as defined, other tubular shapes may also be used.

As shown in FIG. 3, the decoupling sleeve 50 may preferably be positioned to float freely in the axial and radial directions in the conduit area as shown within the sleeve 27 or one end may be fixed to permit only slight axial movement. However, in order to maintain uniform fluid flow, the collar 56 is sized to be retained within the sleeve 27, such as by engaging or camming axially beyond a plurality of detents 60 formed at a predetermined retaining location on the forward interior end of the sleeve 27. Other means for retaining the collar 56 and hence the decoupling sleeve 50 may also be used.

When the decoupling sleeve 50 is thus retained within the infusion sleeve 27 as described, the end 58 remote from the collar 56, remains free to float slightly in a radial direction. In addition, the cooperation between the collar 56 and the detent 60 permits slight axial movement of the decoupling sleeve 50.

Figure 5:
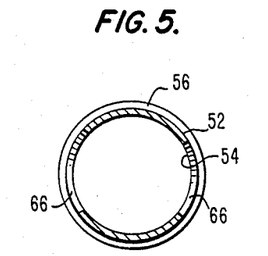
FIG. 5 is a cross-sectional view taken along line 5—5 of FIG. 4.

The sleeve 50 is shown in FIGS. 4 and 5 with a continuous circumferential surface on the tubular member 52 and the collar 56. The continuity of those surfaces may be interrupted, such as by an elongated slot, axially-extending for a portion or for the entire length of the decoupling sleeve 50. A construction wherein a slot is provided along the entire length of the decoupling sleeve 50 may facilitate production by permitting the sleeve 50 to be assembled in a radial direction, rather than in an axial direction as when the surface is continuous.

The decoupling sleeve 50 further includes a plurality of slots 62 having axially-extending portions 64 terminating in a pair of axially-spaced semicircularly-shaped portions 66 defined by a radius centered along an axis of the wall and extending from a location adjacent the collar 56 to another location intermediate the axial length of the wall of the tubular portion 52 of the decoupling sleeve 50. Preferably, a pair of such slots are positioned diametrically opposite each other in the walls of a tubular member 52. However, such slots as understood, may be eliminated, or one or more than two slots may be used. When used, the slots 62 permit fluid passage between the interior and exterior of the decoupling sleeve 50.

The utilization of the decoupling sleeve 50 as shown in FIGS. 4 and 5 in the combination shown in FIG. 3 has provided significant improvement in reducing and eliminating the cavitation and bubbles which may occur during a surgical procedure or during eye surgery. Thus, the ultrasonic action in the eye has been stabilized relative to the ultrasonic action exhibited by the conventional embodiments of FIGS. 1 and 2. While the decoupling sleeve 50 is shown as a component separately installed in the ultrasonic handpiece, it may be combined with the tip cap 26 and sleeve 28, or with the one piece infusion sleeve 27 as shown respectively in the conventional embodiment of FIGS. 1 and 2, or in FIG. 3, to achieve the same function. In that case, for example, the infusion sleeve 28 and the decoupling sleeve 50 are formed as an integral component. In addition, while the decoupling sleeve provides an acceptable portion of fluidic resistance by reducing the flow area in the fluid conduit, the beneficial effects of stabilizion which accrue from the use of the decoupling sleeve 50 outweigh the increased fluidic resistance. Moreover, a reduced flow of irrigating fluid during surgery may prove desirable.

Thus, utilization of the decoupling sleeve 50 in the manner shown has improved the consistency of power transfer and reduced certain of the instability which occurs from the use of the instrument on occasion. While all of the reasons for this improvement are not completely understood, it is believed that the use of the ultrasonic decoupling sleeve 50 according to the invention acts to isolate the surgical tip from the outer shell of the handpiece 11 and positively affect the acoustic coupling in the fluid medium within the irrigation passage, thus affecting the impedance of the fluidic path. In particular, it is believed that the decoupling sleeve 50 serves to increase the mechanical impedance presented to the ultrasonic energy transferred through the fluid medium. The intent is to decouple the ultrasonic action from the exterior of the handpiece to reduce siphoning of power intended to be transferred to the vibrating tip 18. Moreover, the use of the decoupling sleeve 50 acts to isolate the load and confine the acoustical and hydraulic pressure within the handpiece in a favorable way, while reducing sound transmission from the device.

This invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

We claim:

1. An ultrasonic surgical instrument comprising:
   a handpiece,
   a surgical tool supported by said handpiece, and having a distal working end,
   a vibrating means for ultrasonically vibrating said surgical tool,
   a sleeve connected to said handpiece, positioned about a portion of said surgical tool, and defining a coaxial annular irrigation fluid passage through which irrigation fluid can flow from an irrigation fluid supply to a surgical site at said tool,
   a reducing means for reducing cavitation of and bubble formation in the irrigation fluid in said irrigation fluid passage,
   said reducing means comprising an elongated tubular ultrasonic decoupling sleeve positioned in said irrigation fluid passage and a retaining means attached to said decoupling sleeve at a forward location thereof for retaining said decoupling sleeve within said sleeve,
   said retaining means being positioned rearward of said distal working end,
   said retaining means comprising a collar attached to one end of said decoupling sleeve, and said retaining means including at least one detent projecting radially inward from said sleeve and positioned proximally relative to said collar.

2. The instrument of claim 1 including,
said sleeve comprising a tip cap engaging the distal end of said handpiece and a sleeve member connected to the distal end of said tip-cap and extending out therefrom.

3. The instrument of claim 2 including,
said tip cap and said sleeve member being constructed separately, and
said sleeve including a fastening means for fastening said sleeve member to said tip cap.

4. The instrument of claim 2 including,
said tip cap and sleeve member being formed together as a single piece construction.

5. The instrument of claim 1 including,
said handpiece including an aspiration conduit connectable to a source of vacuum.

6. The instrument of claim 1 including,
said decoupling sleeve comprising a tube having a tubular inner surface and a tubular outer surface on the opposite side thereof.

7. The instrument of claim 6 including,
said decoupling sleeve being dimensioned and positioned in said irrigation fluid passage so that the irrigation fluid flows on and along both said inner and outer surfaces.

8. The instrument of claim 6 including,
said decoupling sleeve being dimensioned and positioned in said irrigation fluid passage so that the irrigation fluid flows only on said inner surface and is prevented from flowing on said outer surface.

9. The instrument of claim 6 including,
said decoupling sleeve being dimensioned and positioned in said irrigation fluid passage so that the irrigation fluid flows only on said outer surface and is prevented from flowing on said inner surface.

10. The instrument of claim 1 including,
said decoupling sleeve being made from a rigid or semi-rigid material.

11. The instrument of claim 10 including,
said rigid material being plastic.

12. The instrument of claim 1 including,
said decoupling sleeve floating generally freely in said irrigation fluid passage.

13. The instrument of claim 1 including,
said decoupling sleeve being fixed to permit only slight axial movement in said irrigation fluid passage.

14. The instrument of claim 1 including,
said decoupling sleeve including at least one radial opening therethrough defining an irrigation fluid passage.

15. The instrument of claim 14 including,
said opening comprising a longitudinally-disposed slot.

16. The instrument of claim 14 including,
said opening being disposed at the distal end of said decoupling sleeve.

17. The instrument of claim 14 including,
said at least one radial opening comprising a pair of diametrically-opposed openings.

18. The instrument of claim 1 including,
said detent being positioned axially rearward of said collar.

19. A decoupling sleeve member structurally adapted for location in a surgical instrument having an ultrasonically vibrating surgical tip and a conduit means defining a fluid conduit for flowing irrigation fluid to said surgical tip wherein a portion of said surgical tip extends within said conduit, said decoupling sleeve member comprising:

an axially-extending, relatively thin-walled elongated tubular portion having an outer dimension less than the outer dimension of said fluid conduit so that when said decoupling sleeve member is located in said surgical instrument said tubular portion is positioned in said fluid conduit, and an inner dimension sized to receive therein an axially-extending portion of said surgical tip, a retaining means extending out from said tubular portion generally adjacent the distal end thereof for retaining said tubular portion within said conduit means, said retaining means, when said decoupling sleeve member is located in said surgical instrument, being spaced rearwardly of the distal working end of said surgical tip, said tubular portion having at least one opening passing radially therethrough permitting fluid passage between the interior and exterior of said tubular portion, said tubular portion having a proximal end, and said proximal end, when said decoupling sleeve member is located in said surgical instrument, being sized and secured to float generally freely in said fluid conduit.

20. The decoupling sleeve member of claim 19 including,
said retaining means comprising at least one tab extending radially out from and fixed to said tubular portion.

21. The decoupling sleeve member of claim 19 including,
said tab comprising a collar encircling said tubular portion.

22. The decoupling sleeve member of claim 19 including,
said at least one opening comprising at least two spaced axially disposed openings.

23. The decoupling sleeve member of claim 19 including,
said opening having opposed axially-extending portions terminating at their proximal ends with a rounded portion.

24. The decoupling sleeve member of claim 19 including,
said tubular portion being made of a plastic material.

25. The decoupling sleeve member of claim 19 including,
said tubular portion being cylindrical along generally its entire exterior length.

26. An ultrasonic surgical instrument comprising:
a handpiece,
a surgical tool supported by said handpiece,
a vibrating means for ultrasonically vibrating said surgical tool,
a sleeve connected to said handpiece, positioned about a portion of said surgical tool, and defining a coaxial annular irrigation fluid passage through which irrigation fluid can flow from an irrigation fluid supply to a surgical site at said tool,
a reducing means for reducing cavitation of and bubble formation in the irrigation fluid in said irrigation fluid passage, said reducing means comprising an elongated tubular ultrasonic decoupling sleeve positioned in said irrigation fluid passage and a retaining means for retaining said decoupling sleeve within said sleeve, said decoupling sleeve having a forward end, and said retainng means including a collar attached to said forward end of said decoupling sleeve, and at least one detent projecting radially inward from said sleeve and positioned proximally relative to said collar.

27. The instrument of claim 26 including, said detent being engageable with a rearwardmost surface of said collar.

28. The instrument of claim 26 including, said decoupling sleeve being fixed to permit only slight axial movement in said irrigation fluid passage.

29. The instrument of claim 26 including, said decoupling sleeve floating generally freely in said irrigation fluid passage.

30. An ultrasonic surgical instrument comprising:

a handpiece, a surgical tool supported by said handpiece, and including a longitudinal aspirator conduit extending at least partially therethrough and operatively connectable to a source of vacuum, a vibrating means for ultrasonically vibrating said surgical tool, a sleeve connected to said handpiece, positioned about a portion of said surgical tool, and defining a coaxial annular irrigation fluid passage through which irrigation fluid can flow from an irrigation fluid supply to a surgical site at said tool, a reducing means for reducing cavitation of and bubble formation in the irrigation fluid passage, said reducing means comprising an elongated tubular ultrasonic decoupling sleeve positioned in said irrigation fluid passage and a retaining means for retaining said decoupling sleeve within said sleeve, and said retaining means comprising a collar attached to one end of said decoupling sleeve, and at least one detent projecting radially inward from said sleeve and positioned proximally relative to said collar.

31. The instrument of claim 30 including, said retaining means being attached to said decoupling sleeve at a forward location thereon.

32. The instrument of claim 30 including, said tool having a working distal tool end, and said working distal tool end being positioned spaced forward of said retaining means.

33. The instrument of claim 30 including, said sleeve comprising a tip cap engaging the distal end of said handpiece and a sleeve member connected to the distal end of said tip cap and extending out therefrom, and said tip cap and sleeve member being formed together as a single piece construction.

34. The instrument of claim 30 including, said decoupling sleeve comprising a tube having a tubular inner surface and a tubular outer surface on the opposite side thereof, and said decoupling sleeve being dimensioned and positioned in said irrigation fluid passage so that the irrigation fluid flows on and along both said inner and outer surfaces.

35. The instrument of claim 30 including, said decoupling sleeve being fixed to permit only slight axial movement in said irrigation fluid passage.

36. The instrument of claim 30 including, said decoupling sleeve floating generally freely in said irrigation fluid passage.

37. An ultrasonic surgical instrument comprising:

a handpiece, a surgical tool supported by said handpiece, and having a distal working end, a vibrating means for ultrasonically vibrating said surgical tool, a sleeve connected to said handpiece, positioned about a portion of said surgical tool, and defining a coaxial annular irrigation fluid passage through which irrigation fluid can flow from an irrigation fluid supply to a surgical site at said tool, a reducing means for reducing cavitation of and bubble formation in the irrigation fluid in said irrigation fluid passage, said reducing means comprising an elongated tubular ultrasonic decoupling sleeve positioned in said irrigation fluid passage and a retaining means attached to said decoupling sleeve at a forward location thereof for retaining said decoupling sleeve within said sleeve, said retaining means being positioned rearward of said distal working end, said decoupling sleeve comprising a tube having a tubular inner surface and a tubular outer surface on the opposite side thereof, and said decoupling sleeve being dimensioned and positioned in said irrigation fluid passage so that the irrigation fluid flows only on said inner surface and is prevented from flowing on said outer surface.

38. An ultrasonic surgical instrument comprising:

a handpiece, a surgical tool supported by said handpiece, and having a distal working end, a vibrating means for ultrasonically vibrating said surgical tool, a sleeve connected to said handpiece, positioned about a portion of said surgical tool, and defining a coaxial annular irrigation fluid passage through which irrigation fluid can flow from an irrigation fluid supply to a surgical site at said tool, a reducing means for reducing cavitation of and bubble formation in the irrigation fluid in said irrigation fluid passage, said reducing means comprising an elongated tubular ultrasonic decoupling sleeve positioned in said irrigation fluid passage and a retaining means attached to said decoupling sleeve at a forward location thereof for retaining said decoupling sleeve within said sleeve, said retaining means being positioned rearward of said distal working end, and said decoupling sleeve floating generally freely in said irrigation fluid passage.

39. A surgical instrument comprising: an ultrasonically vibratable surgical tip having a distal working end and an axially-extending portion; a vibrating means for ultrasonically vibrating said surgical tip; and a conduit means defining a fluid conduit for flowing irrigation fluid to said surgical tip wherein a portion of said surgical tip extends within said conduit, wherein the improvement comprises a decoupling sleeve member, said decoupling sleeve member comprising:

an axially-extending, relatively thin-walled elongated tubular portion having an outer dimension less than the outer dimension of said fluid conduit so that said tubular portion is positioned in said fluid conduit, and an inner dimension sized to receive therein said axially-extending portion of said surgical tip, said tubular portion having a distal end, a retaining means extending out from said tubular portion generally adjacent said distal end thereof for retaining said tubular portion within said conduit means, said retaining means being spaced rearwardly of said distal working end of said surgical tip in a direction generally towards said vibrating means, and said tubular portion having at least one opening passing radially therethrough permitting fluid passage between the interior and exterior of said tubular portion.

40. The surgical instrument of claim 39 including, said retaining means comprising at least one tab extending radially out from and fixed to said tubular portion.

41. The surgical instrument of claim 40 including, said tab comprising a collar encircling said tubular portion.

42. The surgical instrument of claim 39 including, said at least one opening comprising at least two spaced axially disposed openings.

43. The surgical instrument of claim 39 including, said opening having opposed axially-extending portions terminating at their proximal ends with a rounded portion.

44. The surgical instrument of claim 39 including, said tubular portion being made of a plastic material.

45. The surgical instrument of claim 39 including, said conduit means comprising a cap member, and said retaining means being retained by said cap member.

46. The surgical instrument of claim 39 including, said tubular portion being cylindrical along generally its entire exterior length.

47. The surgical instrument of claim 39 including, said tubular portion having a proximal end, and said proximal end being sized and secured so as to be able to float generally freely in said fluid conduit.

48. An ultrasonic surgical instrument comprising:

a handpiece, a surgical tool supported by said handpiece, and including a longitudinal aspirator conduit extending at least partially therethrough and operatively connectable to a source of vacuum, a vibrating means for ultrasonically vibrating said surgical tool, a sleeve connected to said handpiece, positioned about a portion of said surgical tool, and defining a coaxial annular irrigation fluid passage through which irrigation fluid can flow from an irrigation fluid supply to a surgical site at said tool, a reducing means for reducing cavitation of and bubble formation in the irrigation fluid passage, and said reducing means comprising an elongated tubular ultrasonic decoupling sleeve positioned in said irrigation fluid passage and a retaining means for retaining said decoupling sleeve within said sleeve, and said retaining means being attached to said decoupling sleeve at a forward location thereon generally away from said vibrating means.

49. An ultrasonic surgical instrument comprising:

a handpiece, a surgical tool supported by said handpiece, and including a longitudinal aspirator conduit extending at least partially therethrough and operatively connectable to a source of vacuum, a vibrating means for ultrasonically vibrating said surgical tool, a sleeve connected to said handpiece, positioned about a portion of said surgical tool, and defining a coaxial annular irrigation fluid passage through which irrigation fluid can flow from an irrigation fluid supply to a surgical site at said tool, a reducing means for reducing cavitation of and bubble formation in said irrigation fluid passage, said reducing means comprising an elongated tubular ultrasonic decoupling sleeve positioned in said irrigation fluid passage and a retaining means for retaining said decoupling sleeve within said sleeve, said tool having a working distal tool end, and said working distal tool end being positioned spaced forward of said retaining means and generally away from said vibrating means.

50. An ultrasonic surgical instrument comprising:

a handpiece having a distal end, a surgical tool supported by said handpiece, and including a longitudinal aspirator conduit extending at least partially therethrough and operatively connectable to a source of vacuum, a vibrating means for ultrasonically vibrating said surgical tool, a sleeve connected to said handpiece, positioned about a portion of said surgical tool, and defining a coaxial annular irrigation fluid passage through which irrigation fluid can flow from an irrigation fluid supply to a surgical site at said tool, a reducing means for reducing cavitation of and bubble formation in said irrigation fluid passage, said reducing means comprising an elongated tubular ultrasonic decoupling sleeve positioned in said irrigation fluid passage and a retaining means for retaining said decoupling sleeve within said sleeve, said sleeve which defines the coaxial annular irrigation fluid passage comprising a tip cap having a distal end engaging said distal end of said handpiece and a sleeve member connected to the distal end of said tip cap and extending out therefrom, and said tip cap and said sleeve member being formed together as a single piece construction.

51. An ultrasonic surgical instrument comprising:

a handpiece, a surgical tool supported by said handpiece, and including a longitudinal aspirator conduit extending at least partially therethrough and operatively connectable to a source of vacuum, a vibrating means for ultrasonically vibrating said surgical tool, a sleeve connected to said handpiece, positioned about a portion of said surgical tool, and defining a coaxial annular irrigation fluid passage through which irrigation fluid can flow from an irrigation fluid supply to a surgical site at said tool, a reducing means for reducing cavitation of and bubble formation in said irrigation fluid passage, said reducing means comprising an elongated tubular ultrasonic decoupling sleeve positioned in said irrigation fluid passage and a retaining means for retaining said decoupling sleeve within said sleeve, and said decoupling sleeve being fixed to permit only slight axial movement in said irrigation fluid passage.

52. An ultrasonic surgical instrument comprising:
a handpiece,
a surgical tool supported by said handpiece, and including a longitudinal aspirator conduit extending at least partially therethrough and operatively connectable to a source of vacuum, a vibrating means for ultrasonically vibrating said surgical tool,
a sleeve connected to said handpiece, positioned about a portion of said surgical tool, and defining a coaxial annular irrigation fluid passage through which irrigation fluid can flow from an irrigation fluid supply to a surgical site at said tool,
a reducing means for reducing cavitation of and bubble formation in said irrigation fluid passage, and
said reducing means comprising an elongated tubular ultrasonic decoupling sleeve positioned in and floating generally freely in said irrigation fluid passage and a retaining means for retaining said decoupling sleeve within said sleeve.

* * * * *

UNITED STATES PATENT AND TRADEMARK OFFICE
CERTIFICATE OF CORRECTION

PATENT NO. : 4,816,017
DATED : March 28, 1989
INVENTOR(S) : Hood, et al

It is certified that error appears in the above-identified patent and that said Letters Patent is hereby corrected as shown below:

Title Page, Related U.S. Application Data: delete "Division" and insert
—Continuation—

Column 1, Line 4: delete "divisional" and insert —continuation—

Signed and Sealed this

Thirty-first Day of December, 1996

Attest:

BRUCE LEHMAN

*Attesting Officer*   *Commissioner of Patents and Trademarks*